Feb. 24, 1953 E. S. BOERNER Plant Pat. 1,171
CHRYSANTHEMUM PLANT
Filed April 29, 1952
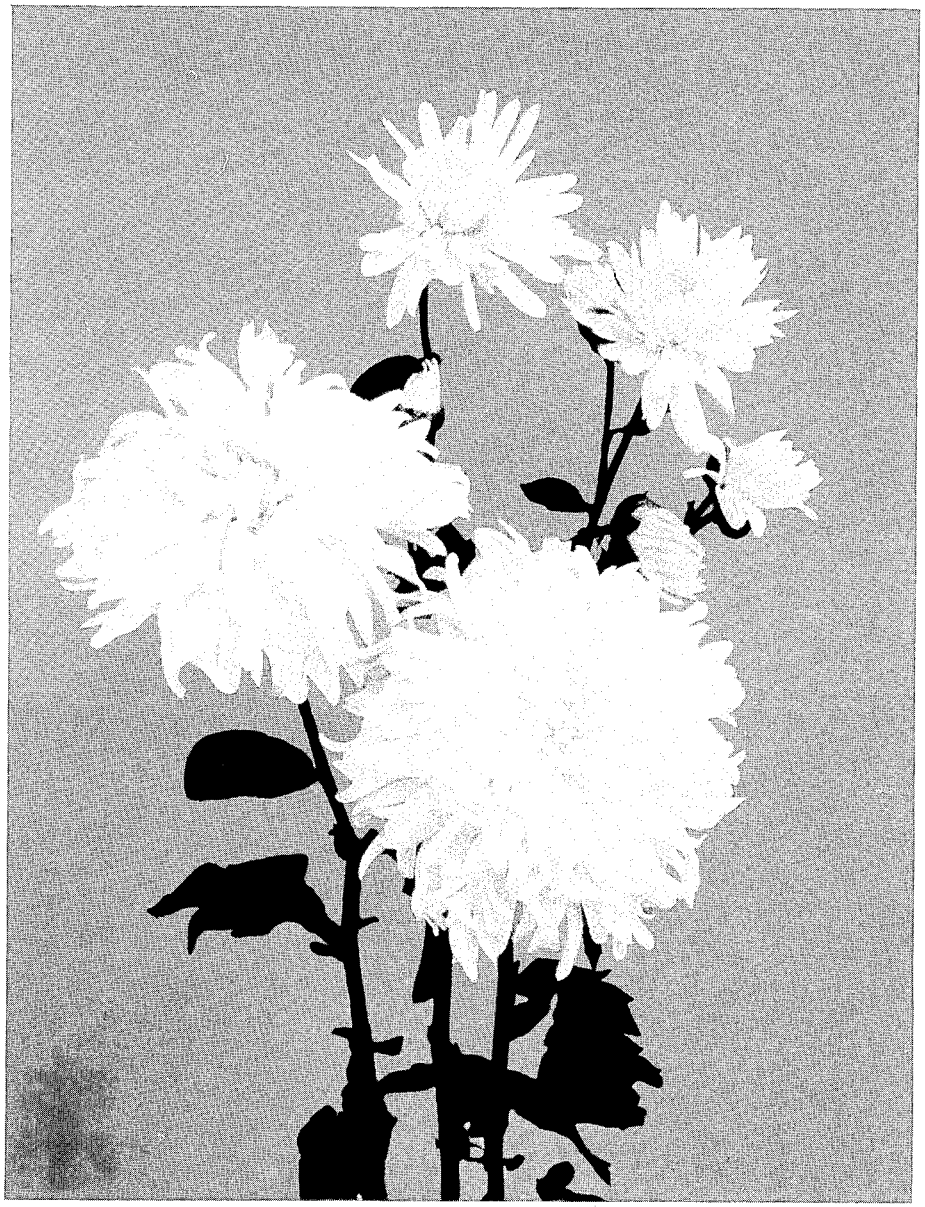
Inventor.
E. S. Boerner
By: Robert Cobb
Attorneys.

Patented Feb. 24, 1953

Plant Pat. 1,171

UNITED STATES PATENT OFFICE 1,171

CHRYSANTHEMUM PLANT

Eugene S. Boerner, Newark, N. Y., assignor to Jackson & Perkins Company, Newark, N. Y., a corporation of New York Application April 29, 1952, Serial No. 284,925

1 Claim. (Cl. 47—60)

This invention relates to a new and distinct variety of chrysanthemum plant of the semi-decorative type, which was originated by me by crossing an unnamed and unpatented large-flowered yellow chrysanthemum of the hardy greenhouse type with another unnamed and unpatented variety that is identified in my breeding records by #4499-3 (a pink "Clara Curtis" hybrid).

The primary objective of this breeding was to produce a new variety of chrysanthemum comparable to its large-flowered greenhouse type parent, but which is hardier, more bushy and early-blooming in its habits of growth. This objective was fully achieved, as evidenced by the fact that my new variety blooms in early September, its flowers are large in size and are quite frost-resistant, and the plant is very winter hardy in northern New York, is bushy and has very full growth. The new variety also is characterized by a unique twisting, uneven arrangement of the flower petals at the finish of the open bloom, and which, in combination with the color of the flowers, as hereinafter more particularly described, together with the characteristics first mentioned above, clearly distinguish this variety from its parents, as well as from all other varieties of chrysanthemums of this class.

Asexual reproduction of the new variety by top cuttings and also by underground runners at Newark, New York, shows that the foregoing characteristics and distinctions come true to form and are established and transmitted through succeeding propagations.

The accompanying drawing shows specimens of my new variety of chrysanthemum, with the flowers and foliage in different stages of development.

The following is a detailed description of my new variety, as grown and observed in fields at Newark, New York, in the early part of the month of September and in the early afternoon, with color terminology in accordance with Ridgway's Color Standards and Nomenclature:

Parentage: An unnamed large-flowered yellow chrysanthemum of the hardy greenhouse type × an unnamed variety consisting of a pink "Clara Curtis" hybrid, identified in my breeding records as #4499-3.

Classification: Semi-decorative type; petals finish uneven, giving a ragged appearance.

Growth: Tall and bushy; attains a height of 3 feet.

Cold resistance: Plant very winter-hardy in northern New York; flowers frost-resistant, as determined by comparison with other varieties grown under comparable conditions.

Blooming habit: In Newark, New York, climatic area, date of start of bloom is about September 1st and continues to a hard freeze.

Bud:

*Color.*—When sepals first divide—Primrose Yellow, Plate 30. When petals begin to unfurl—Naphthalene Yellow, Plate 16. When half blown—inside of petals—Sea-foam Yellow, Plate 31; reverse of petals—Sea-foam Green, Plate 31.

*Peduncle.*—Color—Biscay Green, Plate 17. Strength—strong.

Bloom:

*Size.*—4 to 4½ inches.

*Stems.*—Strong; normal.

*Form.*—Semi-decorative.

*Petalage.*—Double.

*Color.*—Center of flower—Martius Yellow, Plate 4. Outer petals—Sea-foam Yellow, Plate 31. Base of petals—Clear Dull-Green Yellow, Plate 17. Inside of petals—Sea-foam Yellow, Plate 31. Reverse of petals—Sea-foam Yellow, Plate 31.

*Petals.*—Texture—thick. Form — long and petals finish uneven, giving a ragged appearance.

Fragrance: Characteristic chrysanthemum.

Plant:

*Form.*—Upright.

*Growth.*—Vigorous; free and full.

Foliage:

*Size.*—Medium.

*Quantity.*—Normal.

*Color.*—Upper side—Empire Green, Plate 32. Reverse side—Cress Green, Plate 31.

*Texture.*—Leathery.

I claim:

A new and distinct variety of chrysanthemum plant of the semi-decorative type, substantially as herein shown and described, characterized particularly as to novelty by its bushy, full, winter-hardy and early-blooming habits of growth, by the relatively large size and improved frost resistance of its flowers, and by the distinctive color and habit of its flowers tending to cause the flower petals to assume a twisted and uneven form at the finish of the bloom, thereby giving the flowers a ragged appearance.

EUGENE S. BOERNER.

No references cited.